(12) United States Patent
Schattke

(10) Patent No.: US 8,888,987 B2
(45) Date of Patent: Nov. 18, 2014

(54) GAS SENSOR TESTING DEVICE

(75) Inventor: Nathan C Schattke, Yorkville, IL (US)

(73) Assignee: Empire Technology Development LLC, Wilmington, DE (US)

( * ) Notice: Subject to any disclaimer, the term of this patent is extended or adjusted under 35 U.S.C. 154(b) by 111 days.

(21) Appl. No.: 13/063,379

(22) PCT Filed: Nov. 9, 2010

(86) PCT No.: PCT/US2010/055961
§ 371 (c)(1),
(2), (4) Date: Mar. 10, 2011

(87) PCT Pub. No.: WO2012/064322
PCT Pub. Date: May 18, 2012

(65) Prior Publication Data
US 2012/0111738 A1    May 10, 2012

(51) Int. Cl.
*G01N 27/26* (2006.01)
*G01N 33/00* (2006.01)

(52) U.S. Cl.
CPC .................................... *G01N 33/007* (2013.01)
USPC ............................ 205/775; 204/430; 204/431

(58) Field of Classification Search
USPC .............. 205/628, 788, 781, 782, 783.5–785, 205/787; 204/410, 411, 421–432, 157.52, 204/157.5, 421–43
See application file for complete search history.

(56) References Cited

U.S. PATENT DOCUMENTS

| | | | |
|---|---|---|---|
| 3,001,918 A * | 9/1961 | Czuha, Jr. ..................... 205/788 |
| 3,081,250 A * | 3/1963 | Hall et al. ..................... 204/430 |
| 4,083,765 A * | 4/1978 | Lawson ......................... 205/788 |
| 4,151,739 A | 5/1979 | Breuer et al. |
| 4,384,925 A | 5/1983 | Stetter et al. |
| 4,900,422 A | 2/1990 | Bryan et al. |
| 5,281,314 A * | 1/1994 | Yagi et al. ..................... 205/788 |

(Continued)

FOREIGN PATENT DOCUMENTS

CN    101261244    9/2008
CN    101261244 A    9/2008

(Continued)

OTHER PUBLICATIONS

PCT International Search Report PCT/ISA/210.

(Continued)

*Primary Examiner* — Luan Van
*Assistant Examiner* — Maris R Kessel
(74) *Attorney, Agent, or Firm* — Moritt Hock & Hamroff LLP; Steven S. Rubin, Esq.

(57) ABSTRACT

Techniques are generally described for a gas sensor testing device. In some examples, the gas sensor testing device comprises a chamber including a wall having an inside surface and an outside surface, the inside surface defining a gas channel, the wall including at least one water molecule. In some examples, the gas sensor testing device includes a first electrode wire coupled to the outside surface of the wall. In some examples, the gas sensor testing device includes a second electrode wire coupled to the inside surface of the wall. In some examples, the wires are operable to generate a current through the wall when a voltage is applied across the wires. In some examples, the current is effective to electrolyze the at least one water molecule to generate a gas.

19 Claims, 2 Drawing Sheets

(56) References Cited

U.S. PATENT DOCUMENTS

| | | |
|---|---|---|
| 6,404,205 B1 | 6/2002 | Kitamura |
| 6,896,781 B1 | 5/2005 | Shen et al. |
| 7,168,288 B2 | 1/2007 | Eickhoff et al. |
| 7,174,766 B2 | 2/2007 | Eickhoff et al. |
| 2003/0082417 A1 | 5/2003 | Lillis |
| 2010/0098997 A1* | 4/2010 | Ohgi et al. ............... 429/33 |

FOREIGN PATENT DOCUMENTS

| | | |
|---|---|---|
| GB | 2291189 | 1/1996 |
| GB | 2291189 A | 1/1996 |
| WO | WO 2008090774 A1 * | 7/2008 |

OTHER PUBLICATIONS

PCT Written Opinion of the International Searching Authority PCT/ISA/220.

"Nafion" retrieved from Wikipedia.org. on Mar. 10, 2011.

Velayutham et al. (2004) "Nafion Based Amperometric Hydrogen Sensor"; Ionics 10: 63-67.

"Gas Sensor Calibration"; http://www.permapure.com/technotes/calibration.pdf, p. 161-173, retreived Apr. 6, 2011.

Peak Scientific Gas Generators; http://www.peakscientific.com/products/view-product?resid=155&from=/products, retreived Apr. 1, 2011.

Grot, W., "Nafion," accessed at http://en.wikipedia.org/wiki/Nafion, accessed on Apr. 20, 2012.

International Search Report and Written Opinion for International Application No. PCT/US2010/055961, mailed on Dec. 22, 2010.

Velayutham, G., et al., "Nafion based amperometric hydrogen sensor," Ionics, 2004, vol. 10, No. 1-2, pp. 63-67.

"Gas Sensor Calibration," http://www.permapure.com/wp/wp-content/uploads/calibration.pdf.

* cited by examiner

GAS SENSOR TESTING DEVICE

BACKGROUND

Unless otherwise expressly indicated herein, none of the material presented in this section is prior art to the claims of this application and is not admitted to be prior art by having been included herein.

Gas sensors may be tested periodically to ensure sensor accuracy and system integrity. One way to know whether a gas sensor's readings are accurate is to expose the sensor to a known amount of testing gas. Once exposed to the known amount of testing gas, the sensor output can be evaluated for accuracy of the readings, and can be evaluated for the proper performance of the sensor's alarms.

SUMMARY

In one example, a gas sensor testing device is described. In some examples, the gas sensor testing device includes a chamber, a first electrode wire, a second electrode wire, and an electric source. In some examples, the chamber includes a wall having an inside surface and an outside surface. In some examples, the inside surface defines a gas channel and the wall includes at least one water molecule. In some examples, the first electrode wire is coupled to the outside surface of the wall. In some examples, the second electrode wire is coupled to the inside surface of the wall. In some examples, the electric source is coupled to the first and second electrode wires. In some examples, the first and second electrode wires are operable to generate a current through the wall when a voltage is applied across the first and second electrode wires. In some examples, the current is effective to electrolyze the at least one water molecule to generate a gas.

In one example, a gas sensor testing system is described. In some examples, the gas sensor testing system includes a chamber, a first electrode wire, a second electrode wire, an electric source, a controller and a device. In some examples, the chamber includes a wall having an inside surface and an outside surface. In some examples, the inside surface defines a gas channel and the wall includes at least one water molecule. In some examples, the first electrode wire is coupled to the outside surface of the wall. In some examples, the second electrode wire is coupled to the inside surface of the wall. In some examples, the electric source is coupled to the first and second electrode wires. In some examples, the electric source and wires are effective to generate a current through the wall. In some examples, the current is effective to electrolyze the at least one water molecule to generate a gas. In some examples, the controller is coupled to the electric source. In some examples, the controller is effective to control an output of the electric source.

In one example, a method for a gas sensor testing device is described. In some examples, the method includes applying a current through a wall of a chamber. In some examples, the wall has an inside surface and an outside surface, the inside surface defining a gas channel, the wall including at least one water molecule. In some examples, the current is effective to electrolyze at least one water molecule to generate a gas. In some examples, the method further includes directing the gas toward the gas sensor.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and other features of this disclosure will become more fully apparent from the following description and appended claims taken in conjunction with the accompanying drawings. Understanding that these drawings depict only some embodiments in accordance with the disclosure and are therefore not to be considered limiting of its scope, the disclosure will be described with additional specificity and detail by reference to the accompanying drawings in which:

Figure 1:
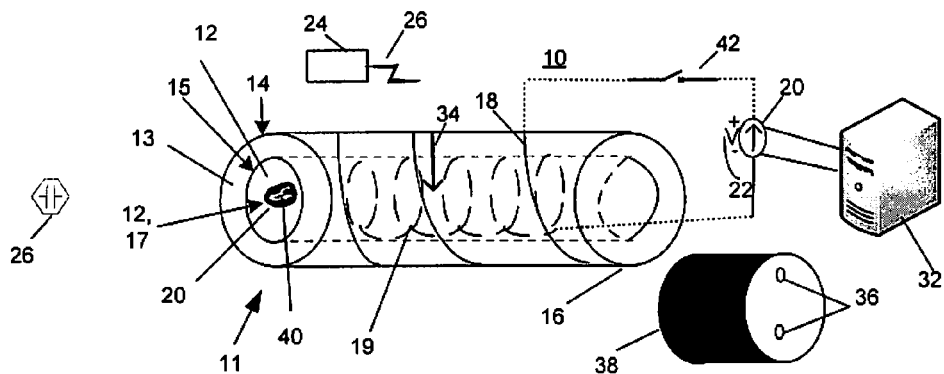
FIG. 1 is a schematic perspective view of an example gas sensor testing device.

all arranged according to at least some embodiments described herein.

DETAILED DESCRIPTION

In the following detailed description, reference is made to the accompanying drawings which form a part thereof. In the drawings, similar symbols typically identify similar components unless context indicates otherwise. The illustrative embodiments described in the detailed description, drawings and claims are not meant to be limiting. Other embodiments may be utilized and other changes may be made without departing from the spirit or scope of the subject matter presented herein. It will be readily understood that the aspects of the present disclosure as generally described herein and as illustrated in the accompanying figures can be arranged, substituted, combined, separated and/or designed in a wide variety of different configurations all of which are explicitly contemplated herein.

This disclosure is generally drawn, inter alia, to devices, apparatus, systems and methods relating to a gas sensor testing device.

Briefly stated, technologies are generally described for a gas sensor testing device. In some examples, the gas sensor testing device comprises a chamber including a wall having an inside surface and an outside surface, the inside surface defining a gas channel, the wall including at least one water molecule. In some examples, the gas sensor testing device includes a first electrode wire coupled to the outside surface of the wall. In some examples, the gas sensor testing device includes a second electrode wire coupled to the inside surface of the wall. In some examples, the wires are operable to generate a current through the wall when a voltage is applied across the wires. In some examples, the current is effective to electrolyze the at least one water molecule to generate a gas.

As described in more detail below, disclosed herein are techniques for implementing a gas sensor testing device. In some examples, the disclosure describes devices, systems and/or methods that may be effective to generate a known amount of hydrogen or oxygen gas over an active surface of a sensor being tested.

Figure 2:
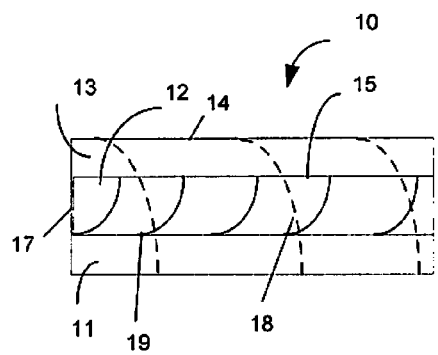
FIG. 2 is a side cut-away view of the gas sensor testing device of FIG. 1.
Figure 3:
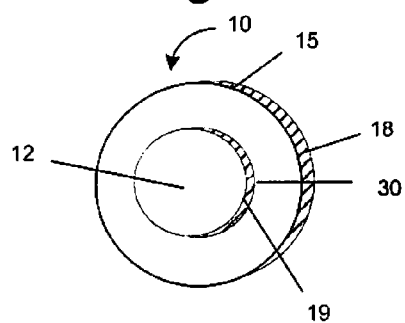
FIG. 3 is a cross sectional view of the gas sensor testing device of FIG. 1.

FIG. 1 is a schematic perspective view of an example gas sensor testing device arranged according to at least some embodiments described herein. FIG. 2 is a side cut-away view of the gas sensor testing device of FIG. 1. FIG. 3 is a cross sectional view of the gas sensor testing device of FIG. 1.

In some examples, a gas testing device 10 may include a chamber 11 such as a polymeric tube surrounding and defining a gas channel 12. In some examples, chamber 11 may correspond to a tube, hollow cylinder, rectangular solid, ellipsoid, cube, sphere or any other shape. In some examples, chamber 11 could be fabricated using integrated circuit or printed circuit fabrication techniques such as microlithography. In these examples, the fabrication techniques may be effective to generate a series of patterns on either side of a sheet of plastic. Fabrication may then include cutting and gluing the plastic to create a desired shape of chamber 11.

Chamber/polymeric tube 11 may include a wall 13 having an outside surface 14, an inside surface 15, a capping end 16, and a gas outlet opening 17. In some examples, capping end 16 may be open and exposed to the ambient environment. In some additional examples, capping end 16 is closed to the ambient environment. A first electrode wire 18 may be coupled to (e.g., directly placed in contact with, or indirectly placed in contact with) the outside surface 14. In some examples, first electrode wire 18 may be coupled to outside surface 14 in a helical pattern as shown in FIG. 1.

In some examples, a second electrode wire 19 may be coupled to (e.g., directly placed in contact with, or indirectly placed in contact with) inside surface 15 of chamber 11. In some examples, first electrode wire 18 and second electrode wire 19 may be vapor deposited or sputtered on surfaces 14, 15. In some examples, first electrode wire 18 and second electrode wire 19 may be made of ink and painted on surfaces 14, 15. The second electrode wire 19 may be coupled to inside surface 15 in a helical pattern as shown in FIG. 1. Both the first electrode wire 18 and the second electrode wire 19 may also be coupled to an electric source 20 such as a voltage or current source. In some examples, the first and second electrode wires 18 and 19 may be coupled to electric source 20 through a switch 42.

In some examples, electric source 20 may be a battery or photovoltaic cell. In some examples, electrical source 20 may be adapted to output alternating current. In some examples, electrical source 20 may be adapted to output direct current. In some examples, electric source 20 may be adapted to output a voltage 22 across the first and the second electrode wires 18, 19. In some examples, voltage 22, along with resistance between first and second electrode wires 18, 19 may result in an electric current 34 travelling through wall 13 of chamber 11. In some examples, as is explained in more detail below, electric current 34 may be effective to electrolyze water molecules absorbed by chamber 11. In some examples, the electrolysis of the water molecules may generate hydrogen and/or oxygen gases 40 in an amount that is proportional to the amount of electricity consumed. Gases 40 may be collected within gas channel 12 of chamber 11. In some examples, either hydrogen or oxygen gas 40 may be used to test a gas sensor. Hydrogen and/or oxygen may be useful for testing hydrogen and/or oxygen sensors and also other sensors as many gas sensors have cross sensitivity to hydrogen, oxygen, or both. An example of gas sensors that may be tested using the techniques herein include, without limitation, hydrogen sensors, oxygen sensors, carbon monoxide (CO) sensors, carbon dioxide ($CO_2$) sensors, and natural gas sensors. In some examples, gases relating to salts, ionic liquids and/or ionic polymers may be tested.

In some examples, chamber 11 may be fabricated at least in part and/or include at least one hydrating polymer. In some examples, all of chamber 11 includes a hydrating polymer. In some examples, a portion of chamber 11 includes a hydrating polymer. Some example polymers are those that are electrically conductive and capable of retaining or absorbing water molecules within and/or on their surface. Some example electrically conductive hydrating polymers include, without limitation, perfluorinated ionomer resins such as ACIPLEX (perfluorosulfonic acid membrane by ASAHI KASEI Corporation), FLEMION (perfluorosulfonic acid-type membranes by ASAHI GLASS Company Ltd.), and NAFION (perfluorosulfonic acid-type membranes by DUPONT). In some examples, chamber 11 may include a salt, ionic liquid, or ionic polymer. In some examples, chamber 11 could include other types of materials such as ionic conductive solid-gel membrane based polyacrylamide hydrogels with a K2CO3 additive, a PEO-based block copolymer and a dissociable lithium salt, an ion implanted polypropylene oxide, and/or a polymer system comprising an anhydride containing polymer and an oxyalkylene amine, etc.

In some examples, electrolysis of the water molecules absorbed by polymeric tube 11 may be effective to generate hydrogen and oxygen gas according to the electrochemical reaction:

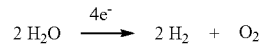

$$2 H_2O \xrightarrow{4e^-} 2 H_2 + O_2$$

In some examples, electrolysis of the water molecules to generate hydrogen and/or oxygen gas results in a depletion of water molecules in polymeric tube 11. Following the reaction, in some examples, the depleted water molecules may be replenished when the hydrating polymer of polymeric tube 11 absorbs additional water molecules from the atmosphere. In this way, gas sensor testing device 10 may be recharged. In some examples, an array of devices 10 may be used so that a user does not have to wait for polymeric tube 11 to recharge after each use.

The length, inside and outside diameters and thickness of polymeric tube 11 may vary as desired. In one example, polymeric tube 11 may have an inside diameter within a range of from about 1 mm to about 2 mm, an outside diameter within a range of from about 2 mm to about 3 mm, a thickness within the range from about 1 to about 2 mm and a length within the range of from about 0.5 cm to about 1.5 cm.

As mentioned above, in some examples, first electrode wire 18 and second electrode wire 19 may be placed in contact with outside and inside surfaces 14 and 15, respectively, of polymeric tube 11. In some examples, both first electrode wire 18 and second electrode wire 19 may be coupled to electric source 20. In one example as shown in FIGS. 1-3, first electrode wire 18 may be wrapped around outside surface 14 of polymeric tube 11 along its length in a helical pattern. In the example, second electrode wire 19 may be wound along inside surface 15 of polymeric tube 11 along its length in a helical pattern. Electrode wires 18 and 19 may be fabricated from any conductive metal or metal alloy including, without limitation, platinum, silver, copper, stainless steel and/or a platinum copper alloy.

As shown best in FIG. 3, in some examples, a layer 30 may be used to adhere first and second electrode wires 18, 19 in electrical contact with outer and inner surfaces 14 and 15, respectively, of chamber 11. In some examples, layer 30 may be an adhesive material or an electrically conductive paste. The same or a different layer 30 may be used respectively for first and second electrode wires 18, 19. In some examples, layer 30 may also absorb moisture, such as water molecules, from the atmosphere and thus promote faster recharging of gas testing device 10 after each use.

In some examples, layer 30 may include metal or metal-modified electrically conductive particles and/or one or more hydrating agents, such as materials that are capable of absorbing water molecules. In some examples, layer 30 may be applied to inside surface 15 and/or outside surface 14 of polymeric tube 11 employing any suitable procedure. An example procedure includes deposition as a flowable viscous material containing one or more solvents, such as water, or an organic solvent, followed by evaporation of the solvents. In some examples, to increase a conductivity and/or a hydrating capability of layer 30, layer 30 may further include one or more multivalent acids such as phosphoric acid. In one example, layer 30 may be a mixture of platinum on carbon, NAFION liquid, phosphoric acid with a solvent such as water or mineral spirits, and the like.

In some examples, gas testing device 10 may additionally include a cap 38 that may be attached at capping end 16 of polymeric tube 11. Cap 16 may be made of a non-conductive material such as a non-conductive synthetic resin. Cap 16 may be secured to polymeric tube 11 in a gas-tight manner employing any suitable arrangement. Example arrangements include, but are not limited to, friction-fit, by a snap-on mechanism, by threaded engagement, tongue and groove, etc. In some examples, cap 16 may include holes 36 that are sized so that first and second electrode wires 18 and 19 may pass through cap 16 for coupling to electric source 20. In some examples, electric source 20 may be placed within cap 16.

In one example of operation, chamber 11 may first be interrogated to determine a water content of polymeric tube 11. In an example, an interrogation pulse voltage 22 may be applied across first electrode wire 18 and second electrode wire 19 from electric source 20.

A device such as a potentiostat 24 may be coupled (as shown by link 26) to electric source 20 and/or polymeric tube 11. In some examples, device 24 may be adapted to compare voltage 22 output by electric source 20 with a current 34 through wall 13 to produce a comparison result signal. The comparison result signal may be used as an indicator of the amount of water absorbed by polymeric tube 11. In an example, for a NAFION polymeric tube, voltage 22 in an interrogation pulse may be within a range from about 50 mV to about 300 mV. In some examples, the interrogation pulse may be about 5 msec and may generate a current of about 1 mA. After the interrogation pulse, a user may wait about one minute before applying a testing voltage as described below.

In an example of operation, after the absorbed water content of polymeric tube 11 has been determined, gas outlet opening 17 may be aligned with, or directed toward, an active surface of a gas sensor 26. Thereafter, a testing voltage 22 may be applied across first and second electrode wires 18 and 19, respectively, to generate electrical current 34 through wall 13. In an example, testing voltage 22 may be a DC step pulse of about 5 volts and last about 20 seconds. In an example, testing voltage 22 may last more than 2 seconds, have a voltage of greater than 1.2 volts and produce a current of at least 100 mA.

In some examples, the flow of electrical current 34 may cause water molecules absorbed by polymeric tube 11 to electrolyze and thereby generate hydrogen and/or oxygen gas 40 as discussed above. Gas 40 may be collected in gas channel 12 and directed toward an active surface of gas sensor 26 through gas outlet opening 17.

In some examples, different voltages or times 22 may be used to generate different amounts of hydrogen or oxygen gas 40 for the same polymeric tube. Testing voltage 22 may vary according to the type of gas sensor 26 being tested. Testing voltage 22 may vary according to the nature of the hydrating polymer and the thickness of the polymeric tube 11. For a polymeric tube 11 fabricated of NAFION, the testing voltage 22 may be in a range from about 3 volts to about 7 volts DC applied for about 20 seconds depending on the tube thickness.

In some examples, a controller 32 may be coupled to electric source 20. Controller 32 may be configured (e.g., via instructions such as software, firmware, etc.) to control voltage and/or current output by electric source 20.

For each type of gas sensor, testing may be performed over several weeks in various operating conditions to ensure the reliability of the gas sensor testing device. The data that may be used for evaluating the performance of the gas sensor testing device include, without limitation, (1) current under different humidity conditions at an interrogation voltage; (2) testing voltage desired for producing a desired response from the sensor; and (3) recovery time for the hydrating polymer to recharge and achieve equilibrium after each testing.

An example of gas sensor testing device 10 may include polymeric tube 11 made of NAFION. In the example, tube 11 may include an inside diameter of about 1 mm, an outside diameter of about 2 mm, a thickness of about 50 μm and a length of about 1 cm. In the example, first and the second electrode wires 18, 19 may be made of platinum. Paste 30 may be made with 20% platinum on VULCAN XC72R carbon particles (from CABOT Corporation) and may be used to coat first and second electrode wires 18 and 19, respectively. This coating may increase the surface area of the electrolysis reaction discussed above. In an example assembly, device 10 may be soaked in water for 24 hours to saturate polymer tube 11 with water.

Table 1 below lists example DC voltages 22 applied and resulting currents 34 for an example polymeric tube 11. The amount of hydrogen gas 40 generated in response to each voltage 22 may be calculated according the following electrochemical equation:

$$2H + 2e^- \rightarrow H_2.$$

TABLE 1

Example applied voltages and resulting DC currents

| | Voltage (volts) | Current (μA) |
|---|---|---|
| 1 | 1.6 | 53 |
| 2 | 2.1 | 100 |
| 3 | 3.1 | 287 |
| 4 | 4.1 | 540 |
| 5 | 6.1 | 1308 |
| 6 | 7.2 | 1770 |

In an example, device 10 may be used to test a CO (carbon monoxide) gas sensor 26. In the example, an original response from the CO sensor was 51.7 μA/ppm, meaning that the CO sensor provides a 51.7 mV signal reading for 100 ppm CO. In the example, gas sensor testing device 10 may be placed near the CO gas sensor with gas outlet opening 17 directed to an active site of the sensor. A 9-volt battery source may be used as electric source 20. Voltage 22 may be approximately 7.7 volts resulting in current 34 in a range from about 145 μA to about 156 μA. In the example, a signal reading in a range of about 24 mV to about 29.7 mV may be generated by the CO gas sensor which corresponds to approximately 50 ppm CO equivalent.

Figure 4:
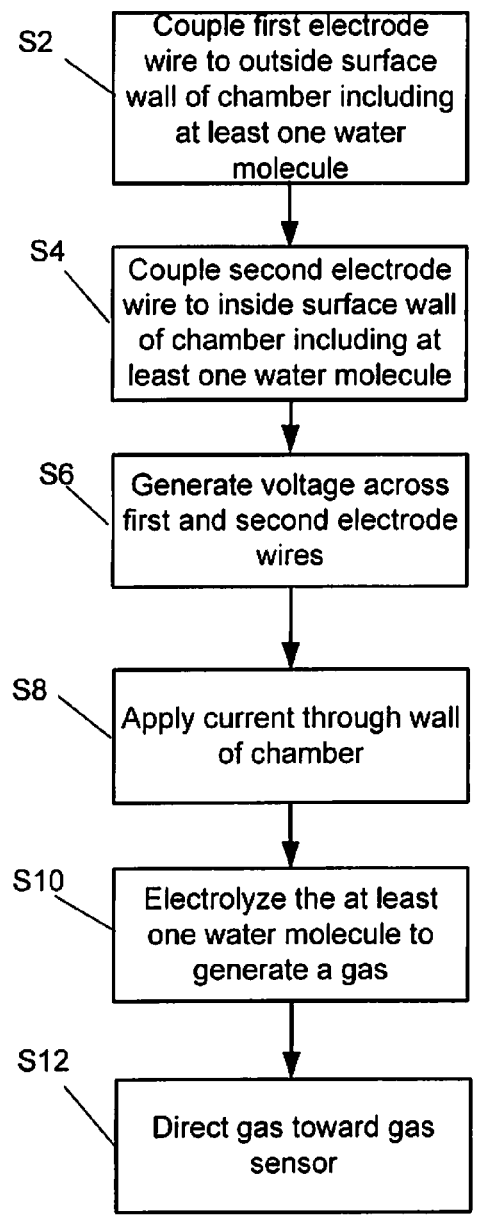
FIG. 4 depicts a flow diagram for example processes for implementing a gas sensor testing device.

FIG. 4 depicts a flow diagram for example processes for implementing a gas sensor testing device arranged according to at least some embodiments described herein. The process in FIG. 4 could be implemented using, for example, device 10 discussed above. An example process may include one or more operations, actions, or functions as illustrated by one or more of blocks S2, S4, S6, S8, S10 and/or S12. Although illustrated as discrete blocks, various blocks may be divided into additional blocks, combined into fewer blocks, or eliminated, depending on the desired implementation. Processing may begin at block S2.

At block S2, a first electrode wire may be coupled to an outside surface wall of a chamber including at least one water molecule. Processing may continue from block S2 to block S4.

At block S4, a second electrode wire may be coupled to an inside surface wall of the chamber including at least one water molecule. Processing may continue from block S4 to block S6.

At block S6, a DC voltage may be generated across the first and second electrode wires. Processing may continue from block S6 to block S8.

At block S8, the voltage and the electrode wires may be configured to apply a DC current through the wall of the chamber. Processing may continue from block S8 to block S10.

At block S10, the current may be effective to electrolyze the at least one water molecule in the wall to generate a gas. Processing may continue from block S10 to block S12. At block S12, the gas may be directed toward a gas sensor.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. A gas sensor testing device comprising:
   a chamber including a wall having an inside surface and an outside surface, the inside surface defining a gas channel, the wall including at least one water molecule;
   a cap attached in a gas-tight manner at a first end of the chamber;
   the wall defining a gas outlet opening at a second end of the chamber;
   a first electrode wire coupled to the outside surface of the wall; and
   a second electrode wire coupled to the inside surface of the wall;
   wherein the first and second electrode wires are operable to generate a current through the wall when a voltage is applied across the first and second electrode wires, and wherein the current is effective to electrolyze the at least one water molecule to generate a gas inside the chamber, where the gas inside the chamber has a volume proportionate to the magnitude of the current and proportionate to a time that the current is applied through the wall.

2. The gas sensor testing device as recited in claim 1, wherein the wall includes one or more of an electrically conductive hydrating polymer, a salt, an ionic liquid or an ionic polymer.

3. The gas sensor testing device as recited in claim 2, wherein the chamber includes at least one perfluorinated ionomer resin.

4. A gas sensor testing system, the system comprising:
   a chamber including a wall having an inside surface and an outside surface, the inside surface defining a gas channel, the wall including at least one absorbed water molecule;
   a cap attached in a gas-tight manner at one end of the chamber;
   the wall defining a gas outlet opening at a second end of the chamber;
   a first electrode wire coupled to the outside surface of the wall;
   a second electrode wire coupled to the inside surface of the wall; and
   an electric source coupled to the first and second electrode wires, and wherein the electric source is effective to generate a voltage across the first and second electrode wire, and wherein the electric source and the wires are effective to generate a current through the wall and wherein the current is effective to electrolyze the at least one water molecule to generate a gas inside the chamber, where the gas inside the chamber has a volume proportionate to the magnitude of the current and proportionate to a time that the current is applied through the wall; and
   a controller coupled to the electric source, wherein the controller is effective to control an output of the electric source.

5. The gas sensor testing device as recited in claim 1, wherein the first and second electrode wires include an electrically conductive material selected from the group consisting of platinum, silver, copper, stainless steel and platinum-copper alloy.

6. The gas sensor testing device as recited in claim 1, wherein the first electrode wire contacts the outside surface in a helical pattern.

7. The gas sensor testing device as recited in claim 1, wherein:
   the first wire is adhered to the outside surface of the wall by a first adhesive layer; and
   the second wire is adhered to the inside surface of the wall by a second adhesive layer.

8. The gas sensor testing device as recited in claim 1, wherein:
   the first electrode wire is painted on to the outside surface; and
   the second electrode wire is painted on to the inside surface.

9. The gas sensor testing device as recited in claim 7, wherein the first adhesive layer is a hydrating electrically conductive paste.

10. The gas sensor testing device as recited in claim 7, wherein the first adhesive layer includes at least one multivalent acid, mixture of platinum on carbon, or phosphoric acid with a solvent.

11. The gas sensor testing device as recited in claim 1, wherein the cap includes a non-electrically conductive material.

12. The gas sensor testing device as recited in claim 11, therein the cap includes at least on hole effective to allow the first electrode wire to pass therethrough.

13. The system as recited in claim 12, wherein the electric source is disposed in the cap.

14. The gas sensor testing device as recited in claim 1, wherein the chamber comprises a tube.

15. The gas sensor testing device as recited in claim 1, wherein the first electrode wire is coupled to the outside surface through vapor deposition or sputtering.

16. The system as recited in claim 4, wherein the electric source is a current source.

17. The system as recited in claim 12, further comprising a device coupled to the first electrode wire and the second electrode wire, wherein when the electric source is operable to generate the voltage, the device is effective to generate a signal in response to the current and the voltage, and wherein the signal is effective to indicate an amount of the gas.

18. A method for a gas sensor testing device, the method comprising:
   providing the gas sensor testing device, wherein the gas sensor testing device comprises a chamber including a wall having an inside surface and an outside surface, the inside surface defining a gas channel, the wall including at least one absorbed water molecule, a cap attached in a gas-tight manner at a first end of the chamber, the wall defining a gas outlet opening at a second end of the chamber, a first electrode wire coupled to the outside surface of the wall, and a second electrode wire coupled to the inside surface of the wall;
   applying a voltage across the first electrode wire and the second electrode wire, wherein the first and second electrode wires are effective to generate a current through the wall when the voltage is applied across the first and second electrode wires, and wherein the current if effective to electrolyze the at least on water molecule to generate a gas inside the chamber, where the gas inside the chamber has a volume proportionate to the magnitude of the current and proportionate to a time that the current is applied through the wall; and
   directing the gas outlet opening of the gas sensor testing device to direct the gas toward a gas sensor.

19. The method as recited in claim 18, further comprising comparing the current with the voltage to generate a signal, wherein the signal is effective to indicate an amount of the gas.

* * * * *

UNITED STATES PATENT AND TRADEMARK OFFICE
CERTIFICATE OF CORRECTION

Page 1 of 2

PATENT NO. : 8,888,987 B2
APPLICATION NO. : 13/063379
DATED : November 18, 2014
INVENTOR(S) : Schattke It is certified that error appears in the above-identified patent and that said Letters Patent is hereby corrected as shown below:

Title Page

On Page 2, in item (56), under "OTHER PUBLICATIONS", in Column 2, Line 5, delete "retreived" and insert -- retrieved --, therefor.

On Page 2, in item (56), under "OTHER PUBLICATIONS", in Column 2, Line 7, delete "retreived" and insert -- retrieved --, therefor.

In the Specification

In Column 1, line 2, below Title, insert -- CROSS-REFERENCE TO RELATED APPLICATION
The present application is a U.S. national stage filing under 35 U.S.C. §371 of International Application No. PCT/US2010/055961, filed on Nov. 9, 2010, the entire contents of which are incorporated herein by reference. --.

In the Claims

In Column 9, Line 5, in Claim 1, delete "one water" and insert -- one absorbed water --, therefor.

In Column 9, Line 43, in Claim 4, delete "wires, and" and insert -- wires, --, therefor.

In Column 10, Lines 14-15, in Claim 10, delete "one multivalent acid, mixture" and insert -- one of a multivalent acid, a mixture --, therefor.

In Column 10, Line 20, in Claim 12, delete "therein the cap includes at least on" and insert -- wherein the cap includes at least one --, therefor.

Signed and Sealed this
Ninth Day of June, 2015

Michelle K. Lee
*Director of the United States Patent and Trademark Office*

CERTIFICATE OF CORRECTION (continued)
U.S. Pat. No. 8,888,987 B2

In Column 10, Line 23, in Claim 13, delete "claim 12," and insert -- claim 4, --, therefor.

In Column 10, Line 32, in Claim 17, delete "claim 12," and insert -- claim 4, --, therefor.

In Column 10, Line 54, in Claim 18, delete "current if" and insert -- current is --, therefor.

In Column 10, Line 55, in Claim 18, delete "least on" and insert -- least one --, therefor.